United States Patent [19]

Drogendijk et al.

[11] Patent Number: 4,823,814
[45] Date of Patent: Apr. 25, 1989

[54] PESSARY

[75] Inventors: Arie C. Drogendijk, Krimpen A/D Ijssel; Cornelis Kruithof, Rotterdam, both of Netherlands

[73] Assignee: Fortune Capital Management B.V., Amsterdam, Netherlands

[21] Appl. No.: 4,100

[22] Filed: Jan. 16, 1987

[51] Int. Cl.[4] .............................................. A61F 5/46
[52] U.S. Cl. .................................. 128/834; 128/836; 128/837
[58] Field of Search ............... 128/127, 129, DIG. 25; 604/892

[56] References Cited

U.S. PATENT DOCUMENTS

| 1,949,863 | 11/1932 | Hay | 128/127 |
|---|---|---|---|
| 2,443,943 | 6/1948 | Young | 128/127 |
| 2,574,767 | 11/1951 | Stubbs | 128/127 |
| 2,875,755 | 3/1959 | Heuboski et al. | 128/127 |
| 2,916,035 | 9/1957 | Jones | 128/127 |
| 3,060,931 | 10/1962 | Clark | 128/127 |
| 3,117,573 | 1/1964 | Snell | 128/127 |
| 3,169,894 | 5/1962 | Monett | 128/127 |
| 3,658,057 | 4/1972 | Cimber | 128/129 |
| 4,200,090 | 4/1980 | Drobish | 128/127 |
| 4,381,771 | 5/1983 | Gabbay | 128/129 |
| 4,402,695 | 6/1983 | Wong | 604/892 |
| 4,427,477 | 1/1984 | Milgrom | 128/127 X |
| 4,516,570 | 5/1985 | Taban | 128/130 |

FOREIGN PATENT DOCUMENTS

| 0006609 | 9/1980 | European Pat. Off. | |
| 1115727 | 5/1968 | United Kingdom | 128/DIG. 25 |
| 1452262 | 10/1976 | United Kingdom | 128/DIG. 25 |

Primary Examiner—Robert A. Hafer
Assistant Examiner—Kevin G. Rooney
Attorney, Agent, or Firm—Cushman, Darby & Cushman

[57] ABSTRACT

Pessary particularly applicable in the treatment of prolapses of internal female sex organs, which pessary is formed by a ring-shaped member constructed of such material or such materials that the ring can be deformed by hand to any given shape and the circumferential dimension of the ring can be increased or decreased to some extent by hand, after which the ring retains the ultimately given shape and circumferential dimension. Preferably the ring (1) consists of a core (4) which has the shape of a spiral of non-resilient nature and a flexible casing (5) enclosing said core (4).

6 Claims, 2 Drawing Sheets

PESSARY

The invention concerns a pessary which is particularly applicable in the treatment of prolapse of the internal female sex organs. Seen from top the pessary is a ring-shaped member of which at the least the outside surface is made of biocompatible material such as a synthetic material. A pessary of this type is generally known by the name "Hodge-pessary".

Prolapses of the internal female sex organs result from laceration or stretching of the supporting connective tissues linking these organs to the pelvic wall. The cause may be attributed to many factors, the most prevalent being hormonal and physical effects of pregnancy and childbirth.

A prolapse may affect various parts of the internal organs, to wit the uterus and the anterior and posterior vaginal walls, taking into account that one as well as several of these parts may be affected. A prolapse of the uterus takes place as a result of weakening of the ligaments which connect it to the pelvic wall. A prolapse of the anterior vaginal wall results from weakening of the supportive tissues located between the bladder and the vagina: the bladder descends and forces the anterior vaginal wall with it.

A prolapse of the posterior vaginal wall may occur in two different spots: proximally due to weakening of the supporting ligaments of the lowest section of the abdominal cavity floor and distally due to dilation of the natural cleft in the pelvic floor muscles. Both types of posterior wall collapse can occur entirely independently of each other.

Prolapses may cause unpleasant sensations in the abdomen and local physical discomfort. Conservative treatment of uterine and anterior vaginal wall prolapses is possible by means of introducing a supportive ring or pessary in the vagina.

The known pessary is manufactured of rigid material such as porcelain, ebonite, a hard plastic material, etcetera. After insertion in the vagina it functions in such manner that the pessary itself lies on the pelvic floor muscles and is thus supported by them. Simultaneously it supports the uterus or anterior vaginal wall either directly through local pressure or indirectly by causing increased tensening of the supportive tissues involved.

As the pessary itself must lean on the pelvic floor muscles, it should be large enough to remain positioned on the cleft in the pelvic floor even with downwardly directed abdominal pressure. However, in case of prolapse, the muscles of the pelvic floor are often flaccid and thereby their cleft is relatively wide, so that then the pessary would descend with the pelvic floor or slip outwardly through the widened cleft. A relatively large pessary, which thereby and by its construction will be of a somewhat resilient nature, does not solve this problem because it would laterally strain the vaginal wall too much or, because of its flexibility, would be pushed out as easily as it is inserted.

If the pelvic floor muscles have not weakened and thereby the cleft is not too wide, a pessary of adequate width cannot be inserted, especially when also the vaginal opening is relatively narrow as this may happen in post-menopause due to involution.

If in case of a major prolapse and wide vaginal cavity a large-sized rigid pessary can be inserted, the uterus and the anterior vaginal wall may yet prolapse through the orifice of the ring.

The known pessary meets only those requirements which are demanded of the pessary by only a few particular individual prolapses, it being noted that the individual anatomical situation depends on five diverse variables, to wit: the individual build of the vagina and its surrounding tissue; the nature and the degree of the prolapse; the condition of the pelvic floor muscles and the width of the vaginal opening.

The object of the invention is to provide a pessary that entirely meets with individual requirements in case of pessary treatment of a prolapse.

This object is attained in that in the pessary according to the invention the ring is manufactured of such material or such materials that it can be deformed by hand to any given shape and the circumferential dimension of the ring can, to some extent, be increased or decreased by hand, after which the ring retains the ultimately given shape and circumferential dimension.

The shape and circumferential dimension of a pessary according to the invention can be perfectly adapted to the individual anatomy, both prior to and after insertion, so that the ring, after being inserted, supports both the neck of the bladder and the uterus but the ring itself is supported as little as possible by the pelvic floor muscles so that the effect of the ring depends much less on the quality of these muscles.

The shape into which the ring should be bent is determined by the anatomical proportions within the vaginal cavity, an impression of which may be obtained e.g. by an internal examination of the vagina. The ring retains the shape and dimension which are ultimately given to it, because the ring has sufficient resistance to deformation due to the pressure exerted by tissues.

Essentially all occuring prolapses can be optimally treated with the pessary according to the invention. Additionally only rings of a few different sizes need be kept available in order to meet the demand from many individual vaginal sizes.

The ring is preferably constructed of a core of stainless steel or similar material, encased in a flexible casing, preferably consisting of silicone rubber.

The core has preferably the shape of a spiral of non-resilient character.

In a ring formed in this way by a specific choice of the gauge of the spirally wound wire and of the spiral diameter in proportion to the ring diameter, the ring can be of sufficient flexibility to enable molding by hand to a permanent shape and circumferential dimension, while the ring still offers sufficient resistance to deformation caused by pressure of tissues. Stainless steel is resistant to influences emanating from the human body and can be reshaped frequently without breaking, while silicone rubber is a flexible material with excellent tissue compatible qualities.

Advantageously the ring, in its initial form as seen from top, has the contour of an egg-shaped oval, while from lateral view, as seen towards the longest dimension, it has the shape of a segment of a circle.

Accordingly constructed the ring, after insertion, can lie with the upwardly directed pointed end behind the cervix, pushing up the posterior vault, while the upwardly directed rounded end can lie behind the publis, from that particular spot pushing the vagina up in the region of the bladder neck, so that the inserted ring leans practically exclusively on the symphysis pubis and the retropubic place of attachment of the pelvic floor muscles and the ring itself is then not mainly supported by the pelvic floor muscles. Moreover, because of the pressure exerted from the abdominal cavity both on the uterus and the posterior vaginal wall and consequently on the more pointed end of the ring, the opposite end of the ring is not pushed toward the vaginal opening, but because of the bow-shape it is pushed further up behind the symphysis so that there is less chance for the ring to be pushed out, whereas in that both ends of the ring extend upwardly within the vagina, chances of hindrance during intercourse are minimal.

Advantageously the ring can be fitted with a diaphragm, also enabling the pessary to serve as contraceptive.

The casing can at the least be partially hollow, the cavity(s) being filled with a liquid or powdered substance consisting preferably of a medication which can be delivered by diffusion to the pessary-user. Additionally the coating can consist partly of a polymer for gradual release of anti-microbial agents, contraceptives or substituting hormones.

The cavity(s) may also contain therapeutic or measuring apparatus for instance electrodes with energy-source for treatment of incontinence by way of muscle-stimulation, or for measuring the tensions of the vaginal or uterine muscles. A transmitter may be provided for wirelessly transmitting the measurements.

The pessary according to the invention may also serve to relieve incontinence in that a strip of an elastic material is arranged on the outside of the ring which strip is fixed along its edges whereas the space between the strip and the ring is in communication with means for pumping a fluid into said space so that the strip is expanded. By pumping air into said space e.g. by pushing in a balloon the strip is expanded so that the urethra is pressed together and closed off.

It is noted that a so-called resilient pessary is known which is formed by an annular endless coiled spring coated by silicon rubber or a plastic material. Thus by the coiled spring said ring has a resilient character so that by a deformation a tension is created in the ring which tends to push the ring back into its initial shape. Therefor a resilient pessary of this type is easily pressed out and gives only little support to the bladder neck.

The invention is elucidated further on the basis of the embodiment shown in the drawing, in which FIG. 1 gives a top view of a pessary according to the invention;

As shown by the figures, the pessary according to the invention comprises a ring 1 which as seen from top is formed like an egg-shaped oval, as a result of which the ring has a more pointed end 2 and a rounder end 3.

Figure 2:
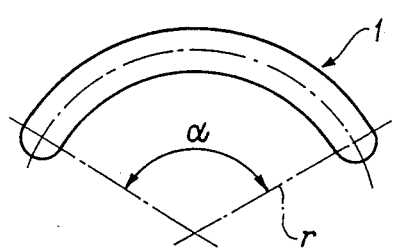
FIG. 2 shows a pessary in side view.

In side elevation as shown in FIG. 2 the ring is shaped like a segment of a circle with a radius r and an included angle of preferably 120°.

Figure 3:
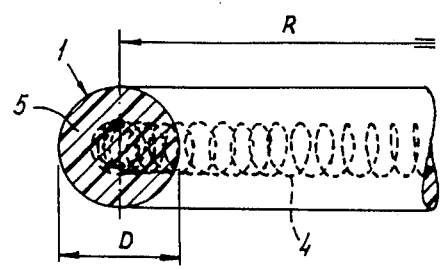
FIG. 3 is a cross section on a larger scale along line III—III in FIG. 1.

As shown in FIG. 3, the ring consists of a spiral-shaped core 4 of stainless steel and a casing 5 of silicone rubber enclosing said core. The silicone rubber may be pigmented so as to offer an esthetic flesh-colored aspect. The silicone rubber can moreover be impregnated with silicone oil, resulting in a lubricated outer surface.

In order to meet the large individual differences and proportions of the vaginal cavity, rings are available of varying nominal diameters R, for instance a series of rings which, starting with the smallest ring of R=50 mm runs up to the largest ring of R=90 mm, the width D increasing stepwise from 6 mm to 12 mm.

Figure 1:
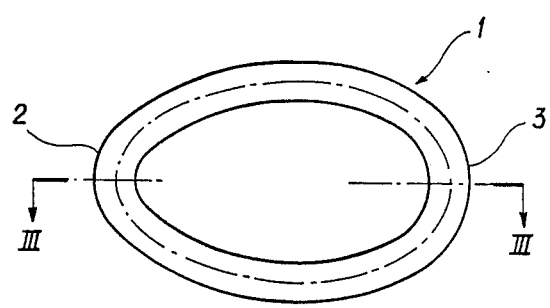
Figure 4:
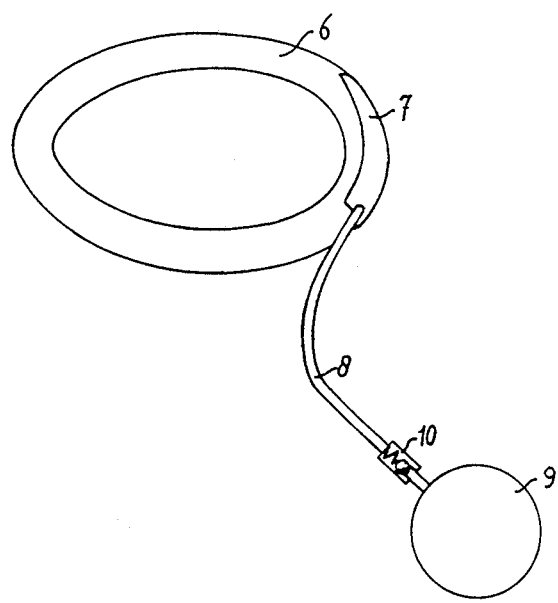
FIG. 4 shows a pessary for relieving incontinence.

As shown by FIG. 4, a ring-shaped pessary 6 of the type illustrated in the FIGS. 1–3 is provided with a strip 7 of an elastic material e.g. silicone rubber which is fixed along its circumferential edges to the outside of the ring so that a slit-shaped space is formed between the inner side of the strip 7 and the ring. Said space is in communication with a balloon 9 through tube 8 in which a non-return valve 10 is provided.

The pessary 6 is inserted in the vagina so that the strip 7 lies close to the urethra. By pressure on the balloon 9 a fluid is pumped into the slit-shaped space whereby the strip 7 is expanded outwardly and the urethra is pressed together and closed off. By operating the valve 10 the fluid is allowed to escape. Women who suffer from incontinence can regulate their urine release in this manner.

We claim:

1. A pessary for treating prolapses of the female sex organs comprising a ring member comprising an outer biocompatible deformable material and a helically-shaped, non-resilient inner core member, said ring member being capable of being deformed by hand into various shapes, the circumferential dimension of said ring member being capable of being changed by hand to increase or decrease said circumferential dimension, and said ring member being capable of retaining the shape and circumferential dimension into which said ring member has been deformed or adjusted by hand.

2. The pessary according to claim 1, wherein said biocompatible flexible material is silicone rubber.

3. The pessary according to claim 1, wherein said ring member further comprises a hollow portion.

4. The pessary according to claim 3, wherein said hollow portion is bounded on the exterior by a semi-permeable membrane and contains a fluid or powder medication.

5. The pessary according to claim 1, wherein said ring member, prior to any deformation, has an egg-shaped oval top view.

6. The pessary according to claim 1, wherein said ring member, prior to any deformation, has the shape of a segment of circle as viewed from the side perpendicular to the long axis.

* * * * *